US007638308B2

(12) United States Patent
Choi et al.

(10) Patent No.: US 7,638,308 B2
(45) Date of Patent: Dec. 29, 2009

(54) DIAGNOSIS METHOD AND KITS FOR INHERITED NEUROPATHIES CAUSED BY DUPLICATION OR DELETION OF CHROMOSOME 17P11.2-P12 REGION

(75) Inventors: Byung Ok Choi, Seoul (KR); Ki Wha Chung, Daejeon (KR)

(73) Assignees: Kongju National University Industry Academia Cooperation Group, Chungeheongam-Do (KR); Ewha University-Industry Collaboration Foundation, Seoul (KR)

( * ) Notice: Subject to any disclaimer, the term of this patent is extended or adjusted under 35 U.S.C. 154(b) by 332 days.

(21) Appl. No.: 10/589,328

(22) PCT Filed: Jul. 6, 2005

(86) PCT No.: PCT/KR2005/002170

§ 371 (c)(1),
(2), (4) Date: Aug. 14, 2006

(87) PCT Pub. No.: WO2006/011716

PCT Pub. Date: Feb. 2, 2006

(65) Prior Publication Data

US 2007/0134672 A1    Jun. 14, 2007

(30) Foreign Application Priority Data

Jul. 7, 2004   (KR) .................... 10-2004-0052652

(51) Int. Cl.
 *C12Q 19/34*  (2006.01)
 *C12Q 1/68*  (2006.01)
(52) U.S. Cl. .......................................... 435/91.2; 435/6
(58) Field of Classification Search ...................... None
See application file for complete search history.

(56) References Cited

U.S. PATENT DOCUMENTS

| 5,306,616 | A | 4/1994 | Lupski et al. |
| 5,645,993 | A | 7/1997 | Chance et al. |
| 5,780,223 | A | 7/1998 | Lupski et al. |
| 6,110,670 | A | 8/2000 | Van Broeckhoven et al. |

OTHER PUBLICATIONS

Lupski et al. Cell 1991 vol. 66: 219-232.*
Suter et al. (2003) Nature Reviews /Neuroscience vol. 4 pp. 714-726.*
Thiel et al. (2002) European Journal of Human Genetics vol. 11: pp. 170-178.*
Gyapay et al. (1994) Nature Genetics vol. 7 pp. 246-249 and 319.*
Gerken et al. (1995) Am. J. Hum. Genet. 56 (2), 484-499.*
Vance JM, et al., Localization of Charcot-Marie-Tooth disease type 1a (CMT1A) to chromosome 17p11.2, In: Genomics, Apr. 1991, vol. 9(4), pp. 623-628. (ISR) Enclosed.
Kim SM, et al., Hereditary neuropathy with liability to pressure palsies (HNPP) patients of Korean ancestry with chromosome 17p. 11.2-p12 deletion, In: Exp Mol Med., Feb. 29, 2004, vol. 36(1), pp. 28-35. (ISR) Enclosed.
Berger P., Young P., Suter U. Neurogenet. 4: 1-15 (2002). Spec-to follow.
Sereda M.W., Horste G.M., Suter U., Uzma N., Nave K.-A. Nature Genet. 9: 1533-1537 (2003) Spec-to follow.
Passage E., Norreel J.C., Noach-Fraissignes P., Sanguedolce V., Pizant J., Thirion X., Robaglia-Schlupp A., Pellissier J.F., Fontes M. Nature Genet. 10: 396-401 (2004) Spec-to follow.
Mersiyanova I.V., Ismailov S.M., Polyakov A.V., Dadali E.L., Fedotov V.P., Nelis E., et al. Human Mutat. 15: 340-347 (2000) Spec-to follow.
Yoshihara T., Yamamoto M., Doyu M., Misu K.I., Hattori N. Hasegawa Y., Mokuno K., Mitsuma T., Sobue G. Hum. Mutat. 16: 177-178 (2000) Spec-to follow.
Numakura C., Lin C., Ikegami T., Guldberg P., Hayasaka K Human Mutat. 20: 392-398 (2002) Spec- to follow.
Berger P., Young P., Suter U. "Molecular cell biology of Charcot-Marie-Tooth disease," Neurogenet. 4: 1-15 (2002).
Sereda M.W., Horste G.M., Suter U., Uzma N., Nave K. -A. "Therapeutic administration of progesterone antagonist in a model of Charcot-Marie-Tooth disease," Nature Genet. 9: 1533-1537 (2003).
Passage E., Norreel J.C., Noach-Fraissignes P., Sanguedolce V., Pizant J., Thirion X., Robaglia-Schlupp A., Pellissier J.F., Fontes M. "Ascorbic acid treatment corrects the phenotype of a mouse model of Charcot-Marie-Tooth disease," Nature Genet. 10: 396-401 (2004).
Mersiyanova I.V., Ismailov S.M., Polyakov A.V., Dadali E.L., Fedotov V.P., Nelis E., et al. "Screening for Mutations in the Peripheral Myelin Genes PMP22, MPZ and Cx32 (GJB1) in Russian Charcot-Marie-Tooth Neuropathy Patients," Human Mutat. 15: 340-347 (2000).

(Continued)

*Primary Examiner*—Teresa E Strzelecka
*Assistant Examiner*—Suchira Pande
(74) *Attorney, Agent, or Firm*—Collard & Roe, P.C.

(57) ABSTRACT

Disclosed herein are a method and kit for diagnosing hereditary diseases CMT1A and HNPP, caused by duplication and deletion in the chromosome 17p11.2-p12 region. In accordance with the present invention, there is provided a method for diagnosing an inherited neuropathy, comprising, running the PCR amplification using microsatellites present in a chromosome 17p11.2-p12 region as markers and DNA typing the resulting PCR amplification products to determine the presence of duplication and deletion in the corresponding chromosomal region, wherein Multiplex PCR amplification is carried out using 6 loci of D17S921, D17S9B, D17S9A, D17S918, D17S2230 and D17S4A as markers, and DNA-typing of the resulting PCR amplification products is carried out to determine duplication and deletion in the corresponding chromosomal region. In accordance with the method of the present invention, the diagnosis accuracy of detecting duplication and deletion in the chromosome 17p11.2-p12 region is greater than 99.9%.

5 Claims, 3 Drawing Sheets

OTHER PUBLICATIONS

Yoshihara T., Yamamoto M., Doyu M., Misu K.I., Hattori N. Hasegawa Y., Mokuno K., Mitsuma T., Sobue G. "Mutations in the Peripheral Myelin Protein Zero and Connexin32 Genes Detected by non-Isotopic RNase Cleavage Assay and Their Phenotypes in Japanese Patients with Charcot-Marie-Tooth Disease," Hum. Mutat. 16: 177-178 (2000).

Numakura C., Lin C., Ikegami T., Guldberg P., Hayasaka K. "Molecular Analysis in Japanese Patients With Charcot-Marie-Tooth Disease: DGGE Analysis for PMP22, MPZ and Cx32/GJB1 Mutations," Human Mutat. 20: 392-398 (2002).

* cited by examiner

[Fig. 1]
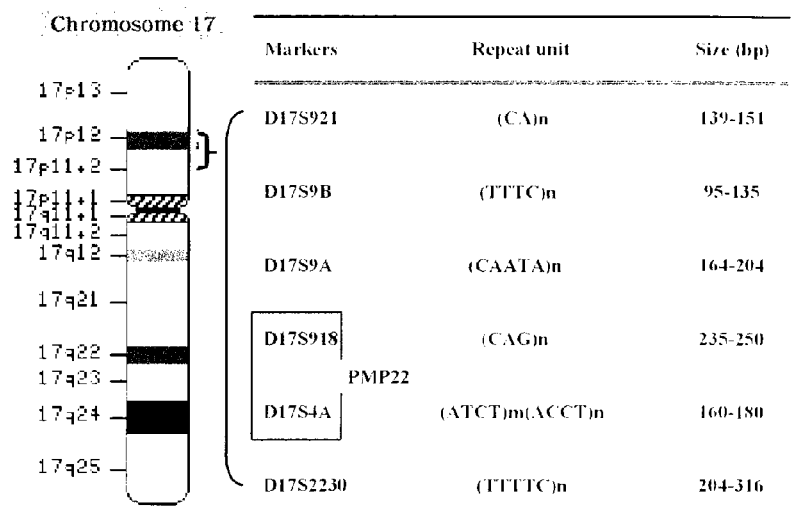
[Fig. 2]
FC44 CMT1 pedigree (control)
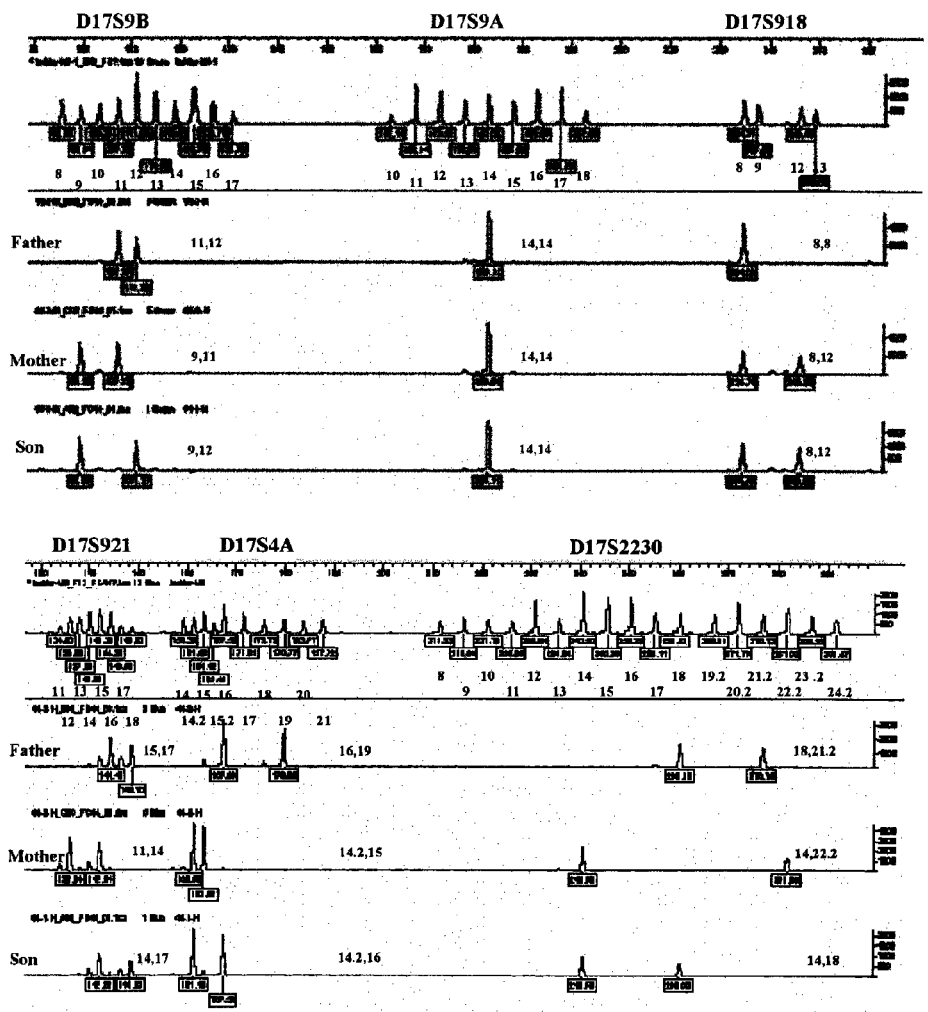

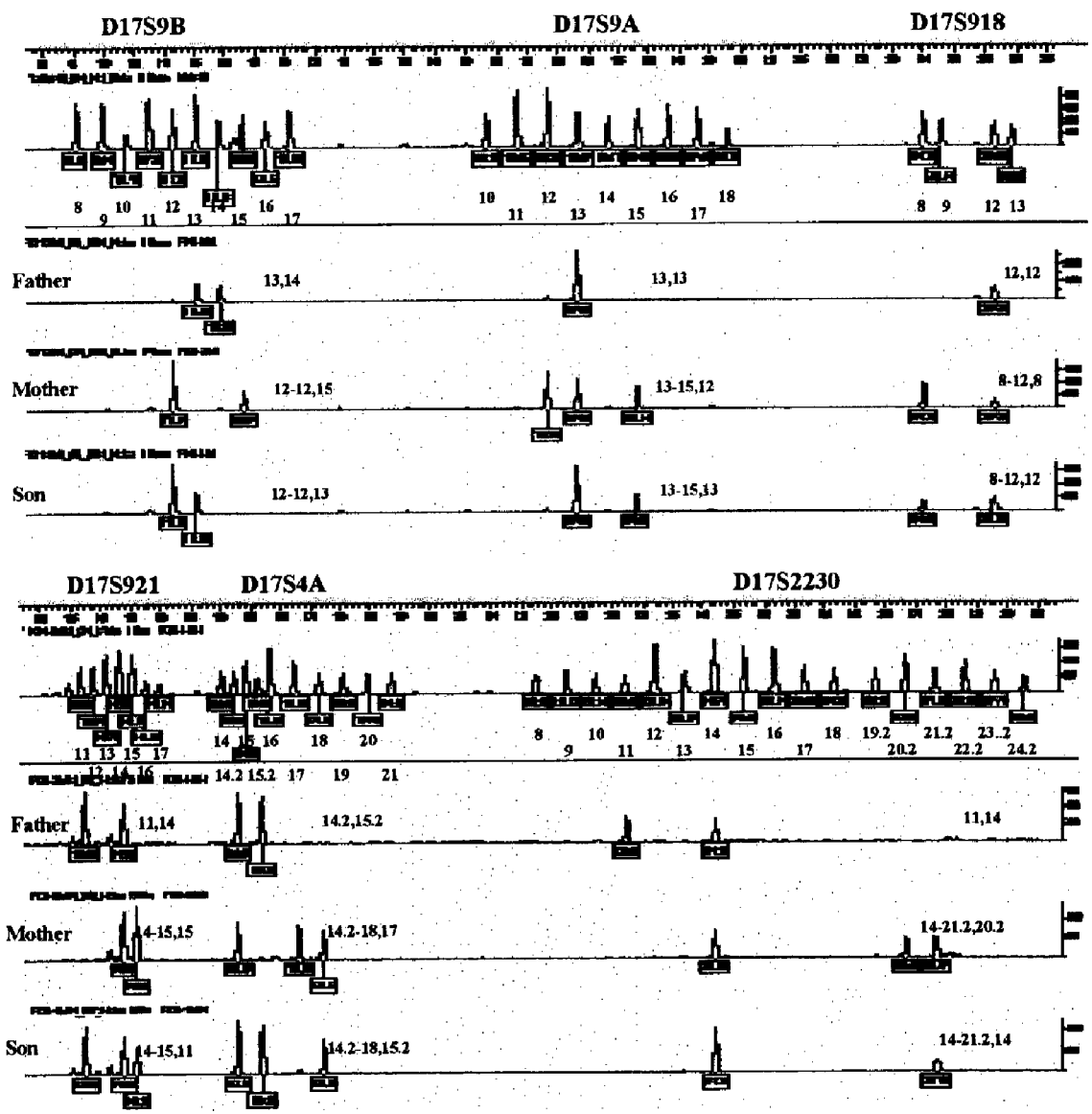
[Fig. 3]

[Fig. 4]
HN123 HNPP pedigree (deletion)
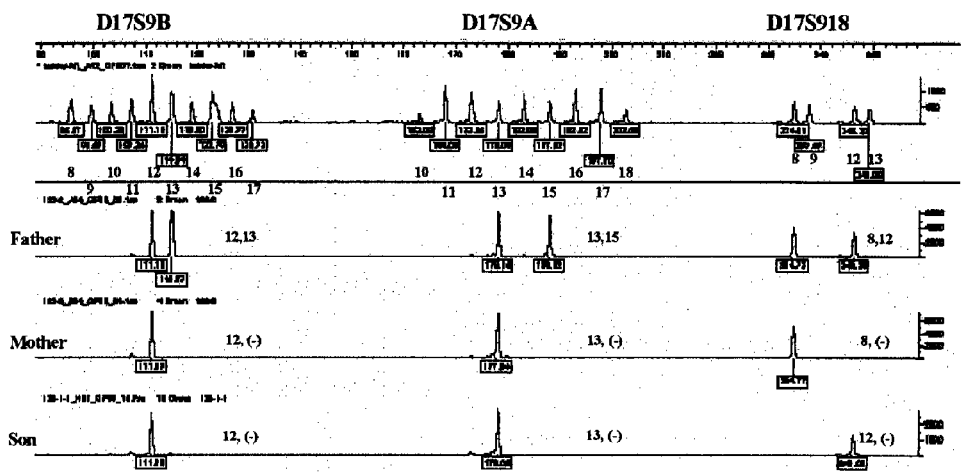
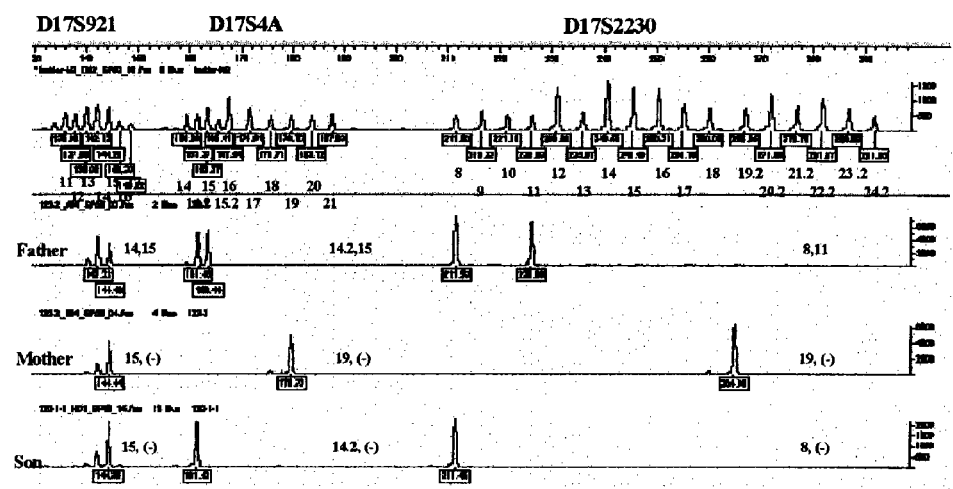
[Fig. 5]
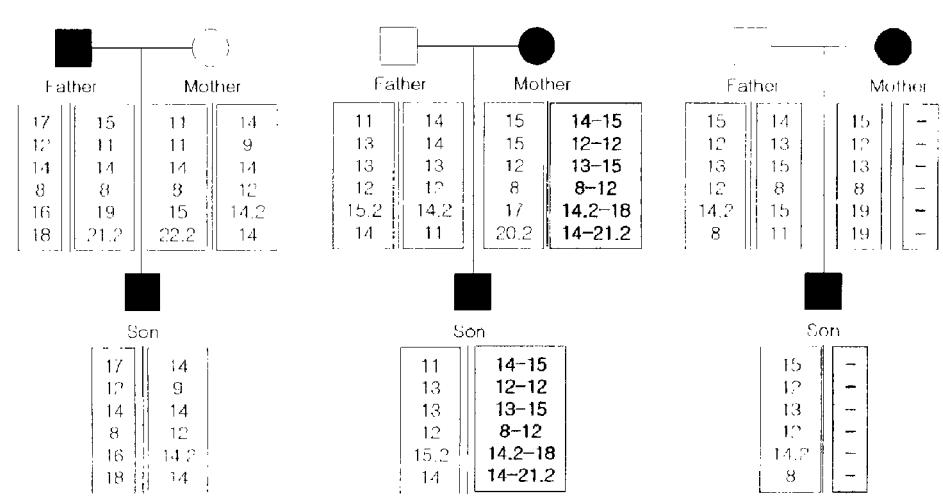

DIAGNOSIS METHOD AND KITS FOR INHERITED NEUROPATHIES CAUSED BY DUPLICATION OR DELETION OF CHROMOSOME 17P11.2-P12 REGION

CROSS REFERENCE TO RELATED APPLICATIONS

Applicants claims priority under 35 U.S.C. §119 of Korean Application No. 10 2004 0052652 filed Jul. 7, 2004. Applicants also claim priority under 35 U.S.C. §365 of PCT/KR2005/002170 filed Jul. 6, 2005. The international application under PCT article 21(2) was published in English.

TECHNICAL FIELD

The present invention relates to a method and kit for diagnosing hereditary diseases CMT1A and HNPP caused by duplication and deletion in the chromosome 17p11.2-p12 region.

BACKGROUND ART

Inherited neuropathy (IN) has a relationship with family medical history and is a congenital disease characterized by dysfunction of motor and sensory nervous systems stemming from gene mutations. Among inherited neuropathies, mention may be made of CMT (Charcot-Marie-Tooth disease), HNPP (Hereditary Neuropathy with liability to Pressure Palsies), DSS (Dejerine-Sottas Syndrome) and CH (Congenital Hypomyelination neuropathy), for example. These diseases are caused by genetically heterogeneous factors, and CMT, exhibiting the highest frequency of occurrence among inherited neuropathies, shows an incidence rate of about 1:2,500 in Europeans, and HNPP shows a frequency of occurrence of 16 people per 100,000.

CMT disease is characterized by muscle weakness and atrophy which gradually progresses primarily in peroneal muscle of the lower extremities. This disease may also manifest areflexia, distal sensory loss, pes cavus, and deafness. Onset primarily occurs in the teens, and rarely after the thirties. However, clinical phenotype and onset age of CMT are very heterogeneous and further it is not easy to perform nerve biopsy for definitive diagnosis, thus rendering accurate diagnosis and treatment difficult (Berger P., Young P., Suter U. Neurogenet. 4: 1-15 (2002)).

Recently, thanks to studies into the human genome and advanced bioinformatics, studies and research to isolate causative genes responsible for hereditary diseases and to elucidate molecular biological mechanisms thereof are now being actively undertaken throughout the world. A great deal of substantial analysis has been made on hereditary causes of CMT, which is known to be developed by hereditary factors, rather than by environmental factors. As a result, more than 10 genes are known to be involved in pathogenesis of CMT, and most of these mutations have been found to be due to Single Nucleotide Polymorphism (SNP) and duplication/deletion of a short base sequence, except for duplication/deletion of 17p11.2-p 12 1.5 Mb. Table 1 below shows inheritance mode and phenotype of important genes responsible for development of CMT known hitherto.

TABLE 1

| Genes | Loci | Inheritance mode | Clinical phenotype | No. of mutation found |
|---|---|---|---|---|
| PMP22 | 17p.11.2 | Autosomal dominant | CMT1, HNPP, DSS, Deafness | 59 |
| Cx32X | Xq13.1 | X-linked dominant | CMT1X | 265 |
| MPZ | 1q22 | Autosomal dominat Autosomal recessive | CMT1B, CMT2, DSS, Deafness | 99 |
| EGR2 | 10p21.1-p22.1 | Autosomal dominant | CMT1 (severe), DSS, CH | 10 |
| NEFL | 8p21 | Autosomal dominant Autosomal recessive | CMT1F, CMT2E | 24 |
| PRX | 10p13.1-p13.2 | Autosomal recessive | CMT1, CMT4F, DSS | 17 |

CMT is broadly classified into CMT1 due to demyelination of the myelin sheath and CMT2 due to an impairment of axon function (axonopathy). More than 50% of CMT1 is caused by a 1.5 Mb duplication in the chromosome 17p11.2-p12 region where a PMP22 (peripheral myelin protein 22) gene is located and the resulting disease is called CMT1A disease, taking the highest proportion among overall CMT disease groups. Contrary to CMT1A, HNPP is reported to be due to deletion of the same 1.5-Mb region in 70% to 100% of patients. Therefore, the presence of duplication in the PMP22 gene enables definitive diagnosis of CMT1A, whereas deletion of the PMP22 gene enables definitive diagnosis of HNPP.

HNPP is an autosomal dominant-hereditary disease accompanied by repetitive neuralgia and muscle weakness. This disease is also associated with nervous system abnormalities induced by partial thickening of the myelin sheath (tomacula) as revealed by nerve biopsy. There are few reported cases of HNPP in Korea, as compared to Western countries, and the reason is considered owing to technical problems in that the presence of tomacula should be confirmed via nerve fiber teasing, in order to make a definitive diagnosis of HNPP disease. However, as it is recently possible to easily diagnose this disease via genetic testing, it is believed that frequency of such disease cases will increase.

Since most diseases that currently receive genetic testing are diseases caused by complicated interaction between polygenic inheritance and various environmental factors, such genetic testing for these diseases simply indicates predisposition to disease pathogenesis (for example, genetic testing of hyperhomocysteinemia-associated MTHFR (5,10-methylenetetrahydrofolate reductase) and breast cancer-inducing BRC-A or BRC-B genes). However, CMT is caused by a single gene mutation, and pathogenesis thereof very faithfully follows Mendelian inheritance even though there are some differences in severity of symptoms. As such, CMT exhibits substantially direct linkage between genetic defects and pathogenesis thereof, as exhibited by Phenylketonuria (PKU) and therefore the results of the genetic testing obtained from such diseases provide a definitive diagnosis, rather than simply at presentation level of predisposition or possibility of disease development, and thus CMT is a genetic disease that is very suitable for utilization of a genetic diagnostic kit. In addition, if the etiologies of inherited neuropathies caused by single gene mutation while exhibiting strong hereditary tendency are elucidated via genetic testing, it will be possible to fulfill underlying treatment of diseases in conjunction with more accurate diagnosis. A need for early diagnosis of inherited neuropathies was not raised hitherto due to the absence of relevant treatment methods even though early diagnosis was made for such inherited neuropathies. However, it was recently published in the scientific literature and scientific journals that ascorbic acid and progesterone antagonists are therapeutically effective on CMT1A (Sereda M. W., Horste G. M., Suter U., Uzma N., Nave K.-A. Nature Genet. 9: 1533-1537 (2003); Passage E., Norreel J. C., Noack-Fraissignes P., Sanguedolce V., Pizant J., Thirion X., Robaglia-Schlupp A., Pellissier J. F., Fontes M. Nature Genet. 10: 396-401 (2004)). Therefore, if methods capable of accurately diagnosing CMT1A duplication/HNPP deletion are developed, inhibition of disease development and patient-tailored treatments may be feasible pursuant to accurate early diagnosis of diseases or diagnosis prior to onset thereof. The present invention relates to accurate diagnosis of CMT1A and HNPP, pathogenic causes of which are duplication and deletion in the chromosome 17p11.2-p12 region.

In order to examine CMT1A duplication and HNPP deletion, conventional methods have employed a southern blotting technique using radioisotopes. Recently, via DNA typing of microsatellites present in a 1.5 Mb duplication/deletion region, it became feasible to examine such chromosomal abnormalities without the use of hazardous radioisotopes. However, since markers such as D17S921, D17S955, D17S839 and D17S122, which are largely used in DNA typing, have sequences consisting of (CA)n repeat units, PCR of such markers causes severe non-specific DNA amplification due to heavy slippage, thus making it difficult to perform accurate typing of microsatellites (Mersiyanova I. V., Ismailov S. M., Polyakov A. V., Dadali E. L., Fedotov V. P., Nelis E., et al. Human Mutat. 15: 340-347 (2000)). As a result, there were disadvantages associated with necessity of utilizing radioisotopes for accurate diagnosis, and inevitable need of parent's samples for examination of patients.

Moleculargenetic studies into inherited neuropathies have been largely led hitherto by European countries, but considerable studies into such diseases are also now being actively undertaken in Japan as well as the USA and European countries since the new millennium. Yoshihara et al. (Yoshihara T., Yamamoto M., Doyu M., Misu K. I., Hattori N., Hasegawa Y., Mokuno K., Mitsuma T., Sobue G. Hum. Mutat. 16: 177-178 (2000)) and Numakura et al. (Numakura C., Lin C., Ikegami T., Guldberg P., Hayasaka K. Human Mutat. 20: 392-398 (2002)) have detected causative mutations in CMT1A duplication, PMP22, MPZ and Cx32 from about 100 Japanese CMT patients. However, there is no accurate statistical data on incidence rate of CMT diseases for Koreans and it is merely believed that situations in Koreans are similar to those of Europeans. The present invention is designed to grasp an accurate definitive diagnosis rate according to a diagnostic method by firstly accurately analyzing hereditary causes of CMT development in Korean CMT patients and their families and comparing the resulting analysis data with foreign data.

DISCLOSURE OF INVENTION

Technical Problem

The present invention relates to diagnosis of CMT1A and HNPP, causes of which are known to be duplication and deletion in the chromosome 17p11.2-p12 region including a PMP22 gene for myelin sheath, respectively.

In the present invention, firstly, samples and clinical data are collected from CMT patient pedigrees and CMT1A duplication and HNPP deletion in patient groups are investigated. Based on these results, relative importance and position of CMT1A duplication and HNPP deletion in onset-diagnosis of overall inherited neuropathies of Koreans, and a rate of definitive diagnosis using the same are provided.

Therefore, the final object of the present invention is to accurately detect duplication and deletion in the chromosome 17p11.2-p12 region, thereby accurately diagnosing CMT1A and HNPP which are caused by duplication and deletion in the 17p11.2-p12 region.

Technical Solution

For the purpose of achieving the above-mentioned objects in accordance with the present invention, new markers including conventional markers are searched and selected as microsatellite markers distributed in the 17p11.2-p12 1.5 Mb region of the short arm of chromosome 17. In particular, as markers such as D17S839 and D17S955, which have been conventionally employed, display 'CA' dinucleotide repeats, PCR amplification thereof leads to heavy slippage. As such, in order to solve such problems and to make accurate diagnosis, the present invention develops and selects new markers having a 3-5 bp repeat sequence, high heterozygosity and various kinds of alleles, among microsatellites present on 17p11.2-p12.

In addition, the present invention constructs primers and constitutes a diagnostic kit, by establishing conditions which enable simultaneous amplification of newly developed markers of interest (Multiplex PCR). Considering overlapping between sizes of PCR amplification products of respective markers, primers are labeled with two kinds of fluorescent dyes and thereby analysis can be carried out by one cycle of PCR amplification and isolation.

Selected markers are amplified by PCR and the resulting amplification samples are rapidly analyzed by an automatic sequencer, followed by DNA typing using GENESCAN and GENOTYPER programs (Applied Biosystems) to accurately detect duplication and deletion in corresponding regions.

Further, the present invention secures experimental data from comparison and analysis between normal persons (more than 100 individuals) and patient's family groups (more than 150 individuals) utilizing samples and clinical data obtained from CMT patient pedigrees, and constructs standard allele ladders for the respective markers, thus ensuring that accuracy of examination for duplication and deletion in the corresponding chromosomal regions can be more than 99.96%.

These and other objects and advantages of the present invention will be described hereinafter and will be more fully understood by reference to the following Examples of the present invention.

In accordance with an aspect of the present invention, the above and other objects can be accomplished by the provision of a method for diagnosing an inherited neuropathy, comprising:

running the Multiplex PCR amplification using microsatellites present in the chromosome 17p11.2-p12 region as markers; and DNA typing the resulting PCR amplification products to determine the presence of duplication and deletion in the corresponding chromosomal region, wherein PCR amplification is carried out using 6 loci of D17S921, D17S9B, D17S9A, D17S918, D17S2230 and D17S4A as markers, and DNA-typing of the resulting PCR amplification products is then carried out to determine duplication and deletion in the corresponding chromosomal region.

Where duplication and deletion in the 17p11.2-p12 region are determined using the above 6 markers, the accuracy thus obtained is greater than 99.96%. Even with use of some of the above-mentioned markers, for example 3 markers, D17S9B, D17S9A and D17S918 alone, the accuracy of diagnosis is more than 97.5%, which is significantly higher than in conventional diagnostic methods. However, it is preferred to use all 6 markers, in order to reduce the rate of misdiagnosis. Herein, 6 markers may be simultaneously PCR-amplified and used (Hexaplex PCR). If necessary, 6 markers may be used sequentially in a two-step manner involving using 3 markers for diagnosis (Triplex PCR) and using the remaining 3 markers if it is difficult to make definitive diagnosis.

In addition, in accordance with the present invention, there are provided primers having base sequences as set forth in SEQ. ID. NOS: 1-12, in which conditions for simultaneous amplification (Multiplex PCR) were established for the above-mentioned markers.

That is, in one embodiment of the present invention, using a mixture in which primers of SEQ. ID. NOS: 1 and 2; primers of SEQ. ID. NOS: 3 and 4; primers of SEQ. ID. NOS: 5 and 6; primers of SEQ. ID. NOS: 7 and 8; primers of SEQ. ID. NOS: 9 and 10; and primers of SEQ. ID. NOS: 11 and 12 were mixed in differential concentrations and a standard allele ladder, the above 6 markers are simultaneously amplified and the resulting amplification products are subjected to DNA typing, thereby determining duplication and deletion in the 17p11.2-p12 region.

In another embodiment of the present invention, the method is carried out in a two-step manner, comprising:

(a) PCR amplification of 3 markers and DNA typing of the resulting PCR amplification products, using a mixture of primers of SEQ. ID. NOS: 3 and 4; primers of SEQ. ID. NOS: 5 and 6; and primers of SEQ. ID. NOS: 7 and 8 in differential concentrations and a standard allele ladder, thereby firstly determining duplication and deletion in the 17p11.2-p12 region; and (b) PCR amplification of the remaining 3 markers and DNA typing of the resulting PCR amplification products, using a mixture of primers of SEQ. ID. NOS: 1 and 2; primers of SEQ. ID. NOS: 9 and 10; and primers of SEQ. ID. NOS: 11 and 12 in differential concentrations and a standard allele ladder, thereby secondly determining duplication and deletion in the 17p11.2-p12 region.

In accordance with another aspect of the present invention, there is provided a kit for diagnosing an inherited neuropathy by determination of duplication and deletion in the chromosome 17p11.2-p12 region, comprising:

a mixture of primers of SEQ. ID. NOS: 1 and 2; primers of SEQ. ID. NOS: 3 and 4; primers of SEQ. ID. NOS: 5 and 6; primers of SEQ. ID. NOS: 7 and 8; primers of SEQ. ID. NOS: 9 and 10; and primers of SEQ. ID. NOS: 11 and 12 in differential concentrations, and a standard allele ladder.

Another form of the diagnostic kit in accordance with the present invention comprises:

a first kit including a mixture of primers of SEQ. ID. NOS: 3 and 4; primers of SEQ. ID. NOS: 5 and 6; and primers of SEQ. ID. NOS: 7 and 8 in differential concentrations and a standard allele ladder; and a second kit including a mixture of primers of SEQ. ID. NOS: 1 and 2; primers of SEQ. ID. NOS: 9 and 10; and primers of SEQ. ID. NOS: 11 and 12 in differential concentrations and a standard allele ladder.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows characteristics of microsatellites distributed in a 1.5 Mb DNA segment of the chromosome 17p11.2-p12 region;

FIG. 2 through 4 show analysis results of PCR products, which were amplified using a diagnosis kit in accordance with the present invention, via an automatic sequencer; and FIG. 5 shows pedigree charts in which patient pedigrees were analyzed using a diagnostic kit in accordance with the present invention.

BEST MODE FOR CARRYING OUT THE INVENTION

Hereinafter, the present invention will be described in more detail with reference to the following Examples including specific experiments and analyzed cases. These examples are provided only for illustrating the present invention and should not be construed as limiting the scope and spirit of the present invention. Therefore, as will be apparently appreciated by those skilled in the art, various modifications, additions and substitutions are possible, without departing from the scope and spirit of the invention as disclosed in the accompanying claims Collection of Patient's Samples and DNA Extraction Therefrom (1) Collection of Samples and Clinical Data from CMT Patient Pedigrees The present invention has collected and analyzed samples from about 150 pedigrees including Korean CMT patients and their families. Samples of patients and their families were those collected from hospitals for about 10 years from the year 1993, while securing clinical manifestations of patients and past medical history of the patient pedigrees. Based on the thus-obtained samples and clinical data, mutual relationship between clinical features of individual patients and genetic mutations was investigated.

(2) Sample Collection and DNA Extraction

Blood or saliva, as a sample, was collected from members of pedigrees of patients suffering from inherited neuropathies, and normal persons (control). After blood was pooled in a tube treated with EDTA, genomic DNA was extracted using a DNA purifier. In addition, DNA extraction from hair roots or saliva of subjects was carried out by treating hair or saliva with Proteinase K at a temperature of 55° C. for 3 hours, followed by phenol:chloroform extraction.

(3) Assessment of FDS (Functional Disability Scale) Due to CMT

In order to determine severity of CMT based on clinical manifestations and the like, the functional handicap was assessed according to a nine-point functional disability scale (FDS) as described by Birouk et al., 1998: 0=normal; 1=normal, but with presence of cramps and fatigability; 2=inability to run; 3=walking difficult but still possible unaided; 4=able to walk with a cane; 5=able to walk with crutches; 6=able to walk with a walker; 7=wheelchair bound; 8=bedridden.

Selection of Markers

In order to exactly detect duplication and deletion in the chromosome 17p11.2-p12 region, new markers, including markers which have been used in studies hitherto, were searched as microsatellite markers distributed in the 17p11.2-p12 1.5 Mb region of the short arm of chromosome 17. In particular, as markers such as D17S839 and D17S955, which have been conventionally employed, contain 'CA' dinucleotide repeats, PCR amplification of such markers thus leads to heavy slippage. Therefore, the present invention has selected 4 kinds of tri-to penta nucleotide markers.

FIG. 1 shows characteristics of microsatellites distributed in a 1.5 Mb DNA segment of the chromosome 17p11.2-p12 region. The present invention has selected markers having high heterozygosity (H≧0.7) and various kinds of alleles, among various microsatellites present on 17p11.2-p12. As a result, microsatellites of 6 loci including D17S921: (CA)n, D17S9B: (TTTC)n, D17S9A: (CAATA)n, D17S918: (CAG) n, D17S2230: (TTTTC)n, and D17S4A: (ATCT)m(ACCT)n were finally selected as markers (See Table 2 below).

Primer Construction and Kit Fabrication (1) Establishing Conditions for Simultaneous Amplification (Multiplex PCR)

For PCR amplification of microsatellite markers, fluorescence-labeled primers were constructed. The primers were designed to have a Tm value of about 60 to 65° C. similar to those of selected markers. Where there were overlaps in sizes of PCR amplification products between respective markers, primers were labeled with two different fluorescent dyes (FAM and HEX). Table 2 below shows respective primer sequences corresponding to the selected markers.

with the same fluorescent materials, genotypes thereof are confirmed on single chromatogram upon analyzing genotypes of such markers.

Genotyping and Diagnosis Utilizing Diagnostic Kit

After PCR was carried out using a diagnostic kit in accordance with the present invention, an isolation system using a single-lane was applied to each sample by means of an automatic sequencer, followed by DNA typing using GENESCAN and GENOTYPER programs.

(1) Application of DNA Diagnostic Kit for Diagnosing CMT1A and HNPP to Patient Pedigrees Using the kit in accordance with the present invention, genetic testing was carried out on 3 families of patients affected with true inherited neuropathies (FC44, FC91, and HN123).

① Clinical Analysis of Analyzed Patient Pedigrees

FC44: 'Mother' and 'offspring (son)' are CMT1 patients; and 'father' is normal.

TABLE 2

| Marker | Repeat unit | Dye-labeling | Length | Primer sequence (5'→3') |
| --- | --- | --- | --- | --- |
| D17S921 | (CA)n | FAM | 139-151 | GTGTTGTATTAGGCAGAGTTCTCC (SEQ. ID. NO. 1) |
|  |  |  |  | GGCAGTAGATGGTGACTTTATGGC (SEQ. ID. NO. 2) |
| D17S9B | (TTTC)n | HEX | 95-135 | TCTCAGTCCTGATTTCTTGATTTTG (SEQ. ID. NO. 3) |
|  |  |  |  | CCAGAGCTAACACCACATTCA (SEQ. ID. NO. 4) |
| D17S9A | (CAATA)n | HEX | 154-204 | CAACCATCAGTGATTTGATGGTTTAC (SEQ. ID. NO. 5) |
|  |  |  |  | GAGTTGTCACTAGAACCCTGTTC (SEQ. ID. NO. 6) |
| D17S918 | (CAG)n | HEX | 235-250 | TCCTGTAATCTGTCCCCAAACGTC (SEQ. ID. NO. 7) |
|  |  |  |  | TTCCTCACACAACCTATTGATAGTC (SEQ. ID. NO. 8) |
| D17S2230 | (TTTTC)n | FAM | 204-316 | AGGAAACTGATGTCTAAAACTATCC (SEQ. ID. NO. 9) |
|  |  |  |  | GTGAATCCAGGAGGCAGAGCTTGC (SEQ. ID. NO. 10) |
| D17S4A | (ATCT)m(ACCT)n | FAM | 116-136 | CTGTGGAGGAAAGAAAACACTGCC (SEQ. ID. NO. 11) |
|  |  |  |  | GCACTAAAGTAGCTTGTAACTCTG (SEQ. ID. NO. 12) |

(2) Construction of PCR Kit

A PCR kit in accordance with the present invention is constructed in the form of a Hexaplex PCR kit that performs simultaneous amplification of 6 markers as listed in Table 2, or a triplex PCR kit that performs simultaneous amplification of 3 respective markers. In addition, experimental data from comparison and analysis between normal persons (n=100) and patient's family groups (n=50), and standard allele ladders for respective markers were prepared such that the accuracy of examination was greater than 99.9%. Preparation of the PCR kits is as follows.

Preparation Example 1

In order to simultaneously amplify all 6 locus markers, i.e., D17S921, D17S9B, D17S9A, D17S918, D17S2230 and D17S4A, a Hexaplex PCR kit was constructed including a mixture of 6 pairs of primers in differential concentrations, wherein the respective primers were represented by SEQ. ID. NOS: 1 through 12.

Preparation Example 2

In this example, a PCR kit was constructed to include Kit A and Kit B as triplex PCR kits, respectively. Kit A includes a mixture of 3 pairs of primers (SEQ. ID. NOS: 3 through 8) labeled with HEX in differential concentrations, in order to amplify markers of 3 loci, i.e., D17S9A, D17S9B and D17S918. Whereas, Kit B includes a mixture of 3 pairs of primers (SEQ. ID. NOS: 1 and 2, 9 through 12) labeled with FAM in differential concentrations, in order to amplify markers of 3 loci, i.e., D17S921, D17S2230 and D17S4A. Since respective 3 markers constituting Kits A and B were labeled FC91: 'Mother', 'offspring 1 (son)' and 'offspring 2 (daughter)' are CMT1 patients; and 'father' is normal.

HN123: 'Father' and 'offspring' are HNPP patients; and 'mother' is normal.

② Diagnostic Kit

Markers obtained from the above-mentioned FC44, FC91 and HN123 patient pedigrees were amplified using a Hexaplex PCR kit including a mixture of 6-paired primers (SEQ. ID. NOS: 1 to 12) and a standard allele ladder, as prepared in Preparation Example 1.

③ Analysis

The resulting PCR amplification products were analyzed using an automatic sequencer (ABI 3100) and genotyping thereof was carried out using GENESCAN and GENOTYPER programs (Applied Biosystems, USA).

④ Results

Results are shown in FIGS. 2 through 5, and Table 3 below.

FIGS. 2 through 4 show analysis result of PCR products amplified by the diagnostic kit in accordance with the present invention, using the automatic sequencer. FIG. 2 shows analysis results of PCR products for CMT1 patient's family (FC 44), thus representing no duplication and deletion in 17p11.2-p12. FIG. 3 shows analysis results of PCR products for CMT1 patient's family (FC 91), thus representing 'duplication' in the corresponding chromosomal region. FIG. 4 shows analysis results of PCR products for HNPP patient's family (HN42), thus representing 'deletion' in the corresponding chromosomal region.

Table 3 below summarizes data of microsatellite genotyping obtained from results of FIGS. 2 through 4.

TABLE 3

| Pedigree No. | Relation | Sex | Phenotype | Microsatellite markers | | | | | | Remark |
|---|---|---|---|---|---|---|---|---|---|---|
| | | | | D17S921 | D17S9B | D17S9A | D17S918 | D17S4A | D17S2230 | |
| FC44 | Father | Male | Affected | 15, 17 | 11, 12 | 14, 14 | 8, 8 | 16, 19 | 18, 21.2 | |
| (CMT1) | Mother | Female | Normal | 11, 14 | 9, 11 | 14, 14 | 8, 12 | 14.2, 15 | 14, 22.2 | |
| | Son | Male | Affected | 14, 17 | 9, 12 | 14, 14 | 8, 12 | 14.2, 16 | 14, 18 | |
| FC91 | Father | Male | Normal | 11, 14 | 13, 14 | 13, 13 | 12, 12 | 14.2, 15.2 | 11, 14 | |
| (CMT1A) | Mother | Female | Affected | 14-15, 15 | 12-12, 15 | 13-15, 12 | 8-12, 8 | 14.2-18, 17 | 14-21.2, 20.2 | duplication |
| | Son | Male | Affected | 14-15, 11 | 12-12, 13 | 13-15, 13 | 8-12, 12 | 14.2-18, 15.2 | 14-21.2, 14 | duplication |
| HN123 | Father | Male | Normal | 14, 15 | 12, 13 | 13, 15 | 8, 12 | 14.2, 15 | 8, 11 | |
| (HNPP) | Mother | Female | Affected | 15, (−) | 12, (−) | 13, (−) | 8, (−) | 19, (−) | 19, (−) | deletion |
| | Son | Male | Affected | 15, (−) | 12, (−) | 13, (−) | 12, (−) | 14.2, (−) | 8, (−) | deletion |

Based on the above analysis results, pedigree charts of 3 families are shown in FIG. 5 (□, ○: Normal; ■, ●: Affected).

The analysis results are summarized according to respective pedigrees as follows.

(a) FC44 Pedigree

When the kit of the present invention was applied, duplication or deletion in the chromosome 17p11.2-p12 region was not observed in this patient family. Therefore, it was determined that pathogenesis of this family was due to mutation in other genes, other than duplication/deletion in the 17p11.2-p12 region.

(b) FC91 Pedigree

From genetic testing via application of the kit in accordance with the present invention, duplication in the 17p11.2-p12 region was observed in 'mother' and 'offspring' of the FC91 patient family. Therefore, 'mother' and 'offspring' were diagnosed as CMT1A patients. In addition, analysis results showed that there was distinctive consistency in "chromosomal duplication-patient relationship", inherited from the patient 'mother' to offspring (patients). As shown in FIG. 5, shaded parts represent duplicated chromosome regions that were found in mother and offspring.

(c) HN123 Pedigree

From genetic testing via application of the kit in accordance with the present invention, deletion in the 17p11.2-12 region was observed in 'mother' and 'offspring' of the HN123 patient family, while duplication or deletion in the corresponding chromosome region was not observed in 'father'. That is, it was confirmed that chromosomal deletion of 'mother' was inherited by offspring, thereby rendering offspring to be HNPP patients.

(2) Investigation into CMT1A Duplication and HNPP Deletion for Korean Patient Groups Duplication in 17p11.2-p12 of chromosome 17 was investigated by genotyping 6 microsatellite markers in 28 families of Korean CMT 1 patients. As a result, segmental duplication of chromosome 17 was observed in 15 families, thus representing a duplication rate of 53.6%. The duplication rate investigated in the present invention shows the results similar to 57.6% (Mostaccicuolo et al. Human Mutat. 18: 32-41 (2001) in Italy, and 53.7% (Mersiyanova et al. Human Mut. 15: 340-347 (2000)) in Russia. In addition, segmental deletion of chromosome 17, which is responsible for HNPP, was observed in 19 families out of the total 24 families, thus representing a deletion rate of 79%.

INDUSTRIAL APPLICABILITY

The present invention enables a diagnosis accuracy of greater than 99.9% in detection of duplication and deletion in the chromosome 17p11.2-p12 region. In addition, in accordance with the present invention, it is possible to make definitive diagnosis of exact hereditary causes for more than 50% of CMT patients and more than 70% of HNPP patients upon first diagnosis using the diagnostic kit in accordance with the present invention, when considering an incidence rate of inherited neuropathies, pathogenic causes of which are duplication and deletion in the chromosome 17p11.2-p12 region. Further, co-application of the diagnostic kit in accordance with the present invention, in conjunction with a diagnostic kit for diagnosing an inherited neuropathy caused by other gene mutations except for duplication and deletion in the chromosome 17p11.2-p12 region, which is another invention of the present inventors, enables a detection rate of more than 90% of total hereditary causes. In addition, the present invention provides an advantage such as no use of radioisotopes by excluding conventional southern blotting. Therefore, the present invention enables exact early diagnosis of inherited neuropathies caused by single gene mutation while exhibiting strong hereditary predisposition via genetic testing, early application of recently-developing treatment methods pursuant to exact diagnosis, and further patient-tailored therapy corresponding to exact etiological causes.

SEQUENCE LISTING

Sequence lists are attached.

The invention claimed is:

1. A method for diagnosing a Charcot-Marie-Tooth disease Type 1A (CMT1A) and Hereditary Neuropathy with liability to Pressure Palsies (HNPP), comprising:
   running PCR amplification using microsatellites present in the chromosome 17p11.2-p12 region as markers; and
   DNA typing the resulting PCR amplification products to determine the presence of duplication and deletion in the corresponding chromosomal region,
   wherein PCR amplification is carried out using at least 3 markers selected from the group consisting of D17S921, D17S9B, D17S9A, D17S918, D17S2230 and D17S4A.

2. The method according to claim 1, wherein PCR is carried out to simultaneously amplify 6 markers, using a mixture of primers of SEQ. ID. NOS: 1 and 2; primers of SEQ. ID. NOS: 3 and 4; primers of SEQ. ID. NOS: 5 and 6; primers of SEQ. ID. NOS: 7 and 8; primers of SEQ. ID. NOS: 9 and 10; and primers of SEQ. ID. NOS: 11 and 12 in differential concentrations and a standard allele ladder.

3. The method according to claim 1, wherein the method includes:
   (a) PCR amplification of 3 markers and DNA typing of the resulting PCR amplification products, using a mixture of primers of SEQ. ID. NOS: 3 and 4; primers of SEQ. ID. NOS: 5 and 6; and primers of SEQ. ID. NOS: 7 and 8 in differential concentrations and a standard allele ladder, thereby firstly determining duplication and deletion in the 17p11.2-p12 region; and
   (b) PCR amplification of the remaining 3 markers and DNA typing of the resulting PCR amplification products, using a mixture of primers of SEQ. ID. NOS: 1 and 2; primers of SEQ. ID. NOS: 9 and 10; and primers of SEQ. ID. NOS: 11 and 12 in differential concentrations and a standard allele ladder, thereby secondly determining duplication and deletion in the 17p11.2-p12 region.

4. A kit for diagnosing a Charcot-Marie-Tooth disease Type 1A (CMT1A) and Hereditary Neuropathy with liability to Pressure Palsies (HNPP), by determination of duplication and deletion in the chromosome 17p11.2-p12 region, comprising:
- a mixture of primers of SEQ. ID. NOS: 1 and 2; primers of SEQ. ID. NOS: 3 and 4; primers of SEQ. ID. NOS: 5 and 6; primers of SEQ. ID. NOS: 7 and 8; primers of SEQ. ID. NOS: 9 and 10; and primers of SEQ. ID. NOS: 11 and 12 in differential concentrations; and
- a standard allele ladder.

5. A kit for diagnosing a Charcot-Marie-Tooth disease Type 1A (CMT1A) and Hereditary Neuropathy with liability to Pressure Palsies (HNPP), by determination of duplication and deletion in a chromosome 17p11.2-p12 region, comprising:
- a first kit including a mixture of primers of SEQ. ID. NOS: 3 and 4; primers of SEQ. ID. NOS: 5 and 6; and primers of SEQ. ID. NOS: 7 and 8 in differential concentrations and a standard allele ladder; and
- a second kit including a mixture of primers of SEQ. ID. NOS: 1 and 2; primers of SEQ. ID. NOS: 9 and 10; and primers of SEQ. ID. NOS: 11 and 12 in differential concentrations and a standard allele ladder.

* * * * *

UNITED STATES PATENT AND TRADEMARK OFFICE
CERTIFICATE OF CORRECTION

PATENT NO. : 7,638,308 B2
APPLICATION NO. : 10/589328
DATED : December 29, 2009
INVENTOR(S) : Choi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 469 days.

Signed and Sealed this

Ninth Day of November, 2010

David J. Kappos
*Director of the United States Patent and Trademark Office*

SEQUENCE LISTING

<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Primer(F)

<400> SEQUENCE: 1
gtgttgtatt aggcagagtt ctcc                                      24

<210> SEQ ID NO 2
<211> LENGTH: 24
<212> TYPE: DNA
<213> ORGANISM: Artificial Sequence
<220> FEATURE:
<223> OTHER INFORMATION: Primer(R)

<400> SEQUENCE: 2
ggcagtagat ggtgacttta tggc                                      24

<210> SEQ ID NO 3
<211> LENGTH: 25
<212> TYPE: DNA
<213> ORGANISM: Artificial Sequence
<220> FEATURE:
<223> OTHER INFORMATION: Primer(F)

<400> SEQUENCE: 3
tctcagtcct gatttcttga ttttg                                     25

<210> SEQ ID NO 4
<211> LENGTH: 21
<212> TYPE: DNA
<213> ORGANISM: Artificial Sequence
<220> FEATURE:
<223> OTHER INFORMATION: Primer(R)

<400> SEQUENCE: 4
ccagagctaa caccacattc a                                         21

<210> SEQ ID NO 5
<211> LENGTH: 26
<212> TYPE: DNA
<213> ORGANISM: Artificial Sequence
<220> FEATURE:
<223> OTHER INFORMATION: Primer(F)

<400> SEQUENCE: 5
caaccatcag tgatttgatg gtttac                                    26

<210> SEQ ID NO 6
<211> LENGTH: 23
<212> TYPE: DNA
<213> ORGANISM: Artificial Sequence
<220> FEATURE:
<223> OTHER INFORMATION: Primer(R)

<400> SEQUENCE: 6
gagttgtcac tagaaccctg ttc                                       23

<210> SEQ ID NO 7
<211> LENGTH: 24
<212> TYPE: DNA
<213> ORGANISM: Artificial Sequence
<220> FEATURE:
<223> OTHER INFORMATION: Primer(F)

<400> SEQUENCE: 7
tcctgtaatc tgtccccaaa cgtc                                      24

<210> SEQ ID NO 8

-continued

```
<211> LENGTH: 25
<212> TYPE: DNA
<213> ORGANISM: Artificial Sequence
<220> FEATURE:
<223> OTHER INFORMATION: Primer(R)

<400> SEQUENCE: 8
ttcctcacac aacctattga tagtc                                              25

<210> SEQ ID NO 9
<211> LENGTH: 25
<212> TYPE: DNA
<213> ORGANISM: Artificial Sequence
<220> FEATURE:
<223> OTHER INFORMATION: Primer(F)

<400> SEQUENCE: 9
aggaaactga tgtctaaaac tatcc                                              25

<210> SEQ ID NO 10
<211> LENGTH: 24
<212> TYPE: DNA
<213> ORGANISM: Artificial Sequence
<220> FEATURE:
<223> OTHER INFORMATION: Primer(R)

<400> SEQUENCE: 10
gtgaatccag gaggcagagc ttgc                                               24

<210> SEQ ID NO 11
<211> LENGTH: 24
<212> TYPE: DNA
<213> ORGANISM: Artificial Sequence
<220> FEATURE:
<223> OTHER INFORMATION: Primer(F)

<400> SEQUENCE: 11
ctgtggagga aagaaaacac tgcc                                               24

<210> SEQ ID NO 12
<211> LENGTH: 24
<212> TYPE: DNA
<213> ORGANISM: Artificial Sequence
<220> FEATURE:
<223> OTHER INFORMATION: Primer(R)

<400> SEQUENCE: 12
gcactaaagt agcttgtaac tctg                                               24
```